(12) United States Patent
Hansen et al.

(10) Patent No.: US 6,558,938 B1
(45) Date of Patent: May 6, 2003

(54) PROTEASE VARIANTS AND COMPOSITIONS

(75) Inventors: Peter Kamp Hansen, Lejre (DK); Peter Bauditz, Soborg (DK); Frank Mikkelsen, Valby (DK); Kim Vilbour Andersen, Copenhagen (DK)

(73) Assignee: Novozymes, A/S, Bagsvaerd (DK)

( * ) Notice: Subject to any disclaimer, the term of this patent is extended or adjusted under 35 U.S.C. 154(b) by 0 days.

(21) Appl. No.: 09/515,150

(22) Filed: Feb. 29, 2000

Related U.S. Application Data

(63) Continuation of application No. PCT/DK98/00360, filed on Aug. 19, 1998.

(30) Foreign Application Priority Data

Aug. 29, 1997 (DK) .......................................... 1997 00987

(51) Int. Cl.[7] .............................. C12N 9/52; C12N 9/54; C12N 15/57; C12N 15/75; C11D 3/386
(52) U.S. Cl. ................. 435/221; 435/69.1; 435/252.31; 435/320.1; 435/471; 536/23.2; 510/306
(58) Field of Search .................. 435/221, 23, 69.1, 435/252.3, 320.1; 536/23.2

(56) References Cited

U.S. PATENT DOCUMENTS

| | | | |
|---|---|---|---|
| RE34,606 E | 5/1994 | Estell et al. | 510/392 |
| 5,352,603 A | * 10/1994 | Vetter et al. | 435/221 |
| 5,543,302 A | 8/1996 | Boguslawski et al. | 435/69.1 |

FOREIGN PATENT DOCUMENTS

| | | |
|---|---|---|
| EP | 0 130 756 A1 | 1/1985 |
| EP | 0 214 435 A2 | 3/1987 |
| EP | 0 251 446 A2 | 1/1988 |
| EP | 0 260 105 B1 | 3/1988 |
| EP | 0 405 901 A1 | 2/1991 |
| EP | 0 525 610 A2 | 2/1993 |
| WO | WO 87/04461 | 7/1987 |
| WO | WO 87/05050 | 8/1987 |
| WO | WO 88/08028 | 10/1988 |
| WO | WO 88/08033 | 10/1988 |
| WO | WO 89/06279 | 7/1989 |
| WO | WO 91/00345 | 1/1991 |
| WO | WO 94/02618 | 2/1994 |
| WO | WO 95/27049 | 10/1995 |
| WO | WO 95/29979 | 11/1995 |
| WO | WO 95/30010 | 11/1995 |
| WO | WO 95/30011 | 11/1995 |
| WO | WO 96/34935 | 11/1996 |
| WO | WO 96/34946 | 11/1996 |

OTHER PUBLICATIONS

Russell et al., Nature, vol. 328, pp. 496–500 (1987).
Thomas et al., Nature, vol. 318, pp. 375–376 (1985).
Russell et al., J. Mol. Biol., vol. 193, pp. 803–813 (1987).
Siezen et al., Protein Engineering, vol. 6, pp. 927–937 (1993).

* cited by examiner

Primary Examiner—Ponnathapu Achutamurthy
Assistant Examiner—William W. Moore
(74) Attorney, Agent, or Firm—Elias J. Lambiris

(57) ABSTRACT

Enzymes produced by mutating the genes for a number of subtilases and expressing the mutated genes in suitable hosts are presented.

The enzymes exhibit improved wash performance in any detergent in comparison to their wild type parent enzymes.

20 Claims, 2 Drawing Sheets

Alignment of subtilases

```
                              1              10             20
                              |              |              |  23
   (BASBPN)    ...........  ........AQ  SVP.......  YGVSQIKAPA  LH.SQGYTGS
   (BLS147)    ...........  .........Q  TVP.......  WGISFINTQQ  AH.NRGIFGN
   (BYSYAB)    ...........  .........Q  TVP.......  WGINRVQAPI  AQ.SRGFTGT
   (BAPB92)    ...........  ........AQ  SVP.......  WGISRVQAPA  AH.NRGLTGS
   (BSSDY)     ...........  ........AQ  TVP.......  YGIPLIKADK  VQ.AQGYKGA
   (TVTHER)    ..........   .YTPNDPYFS  SRQ.......  YGPQKIQAPQ  AW.DIAE.GS
   (BLSAVI)    ...........  ........AQ  SVP.......  WGISRVQAPA  AH.NRGLTGS
   (BSISP1)    MNGEIRLIPY   VTNEQIMDVN  ELP.......  EGIKVIKAPE  MW.AKGVKGK
   (BSEPR)     ...........  .SDGTDTSDN  FEQ.......  WNLEPIQVKQ  AW.KAGLTGK
   (JP170)     LRGLEQIAQY   ATNNDVLYVT  PKPEYEVLND  VARGIVKADV  AQNNFGLYGQ 30             40             50             60
                    | 3234         |              |              |
   (BASBPN)    NVKVAVIDSG  IDSS......  HPDLK..VAG  GASMVPSETN  ...PFQDNNS
   (BLS147)    GARVAVLDTG  IAS.......  HPDLR..IAG  GASFISSEP.  ...SYHDNNG
   (BYSYAB)    GVRVAVLDTG  ISN.......  HADLR..IRG  GASFVPGEP.  ...NISDGNG
   (BAPB92)    GVKVAVLDTG  IST.......  HPDLN..IRG  GASFVPGEP.  ...STQDGNG
   (BSSDY)     NVKVGIIDTG  IAAS......  HTDLK..VVG  GASFVSGES.  ...YNTDGNG
   (TVTHER)    GAKIAIVDTG  VQSN......  HPDLAGKVVG  GWDFVDNDS.  ...TPQNGNG
   (BLSAVI)    GVKVAVLDTG  IST.......  HPDLN..IRG  GASFVPGEP.  ...STQDGNG
   (BSISP1)    NIKVAVLDTG  CDTS......  HPDLKNQIIG  GKNFSDDDGG  KEDAISDYNG
   (BSEPR)     NIKIAVIDSG  ISP.......  HDDLS..IAG  GYSAVSYTS.  ...SYKDDNG
   (JP170)     GQIVAVADTG  LDTGRNDSSM  HEAFRGKITA  LYALGRTNN.  ....ANDPNG 70             80             90            100            110
              646566  |              |  83          |              |              |
   (BASBPN)    HGTHVAGTVA  ALNN.SIGVL  GVAPSASLYA  VKVLG.ADGS  GQYSWIING.
   (BLS147)    HGTHVAGTIA  ALNN.SIGVL  GVRPSADLYA  LKVLD.RNGS  GSLASVAQG.
   (BYSYAB)    HGTQVAGTIA  ALNN.SIGVL  GVAPNVDLYG  VKVLG.ASGS  GSISGIAQG.
   (BAPB92)    HGTHVAGTIA  ALNN.SIGVL  GVAPNAELYA  VKVLG.ASGS  GSVSSIAQG.
   (BSSDY)     HGTHVAGTVA  ALDN.TTGVL  GVAPNVSLYA  IKVLN.SSGS  GTYSAIVSG.
   (TVTHER)    HGTHCAGIAA  AVTNNSTGIA  GTAPKASILA  VRVLD.NSGS  GTWTAVANG.
   (BLSAVI)    HGTHVAGTIA  ALNN.SIGVL  GVAPSAELYA  VKVLG.ASGS  GSVSSIAQG.
   (BSISP1)    HGTHVAGTIA  ANDS.NGGIA  GVAPEASLLI  VKVLGGENGS  GQYEWIING.
   (BSEPR)     HGTHVAGIIG  AKHN.GYGID  GIAPEAQIYA  VKALD.QNGS  GDLQSLLQG.
   (JP170)     HGTHVAGSVL  GNAT..N..K  GMAPQANLVF  QSIMDSGGGL  GGLPANLQTL 120            130            140            150
                     |      125127|              |   146         | 154155
   (BASBPN)    IEWAIANNMD  VINMSLGGPS  G..SAALKAA  VDKAVASG.V  VVAAAAGNEG
   (BLS147)    IEWAINNNMH  IINMSLGSTS  G..SSTLELA  VNRANNAG.I  LLVGAAGNTG
   (BYSYAB)    LQWAANNGMH  IANMSLGSSA  G..SATMEQA  VNQATASG.V  LVVAASGNSG
   (BAPB92)    LEWAGNNGMH  VANLSLGSPS  P..SATLEQA  VNSATSRG.V  LVVAASGNSG
   (BSSDY)     IEWATQNGLD  VINMSLGGPS  G..STALKQA  VDKAYASG.I  VVVAAAGNSG
   (TVTHER)    ITYAADQGAK  VISLSLGGTV  G..NSGLQQA  VNYAWNKG.S  VVVAAAGNAG
   (BLSAVI)    LEWAGNNGMH  VANLSLGSPS  P..SATLEQA  VNSATSRG.V  LVVAASGNSG
   (BSISP1)    INYAVEQKVD  IISMSLGGPS  D..VPELEEA  VKNAVKNG.V  LVVCAAGNEG
   (BSEPR)     IDWSIANRMD  IVNMSLGTTS  D..SKILHDA  VNKAYEQG.V  LLVAASGNDG
   (JP170)     FSQAYSAGAR  IHTNSWGAPV  NGAYTTDSRN  VDDYVRKNDM  TILFAAGNEG
```

Fig. 1

```
            160        170        180                  190
             |          |          |                    |
(BASBPN)  TSGS.SSTVG YPGKYPSVIA VGAVD..... ......SSNQ RASFSSVG..
(BLS147)  RQG.....VN YPARYSGVMA VAAVD..... ......QNGQ RASFSTYG..
(BYSYAB)  AGN.....VG FPARYANAMA VGATD..... ......QNNN RATFSQYG..
(BAPB92)  AGS.....IS YPARYANAMA VGATD..... ......QNNN RASFSQYG..
(BSSDY)   SSGS.QNTIG YPAKYDSVIA VGAVD..... ......SNKN RASFSSVG..
(TVTHER)  NTAP....N. YPAYYSNAIA VASTD..... ......QNDN KSSFSTYG..
(BLSAVI)  AGS.....IS YPARYANAMA VGATD..... ......QNNN RASFSQYG..
(BSISP1)  DGDERTEELS YPAAYNEVIA VGSVS..... ......VARE LSEFSNAN..
(BSEPR)   NGKP....VN YPAAYSSVVA VSATN..... ......EKNQ LASFSTTG..
(JP170)   PGSG...TIS APGTAKNAIT VGATENLRPS FGSYADNINH VAQFSSRGPT 200        210                 220
             |          |                219|221 225
(BASBPN)  ....PELDVM APGVSIQSTL PGNK...... ......YGAY NGTSMASPHV
(BLS147)  ....PEIEIS APGVNVNSTY TGNR...... ......YVSL SGTSMATPHV
(BYSYAB)  ....AGLDIV APGVGVQSTV PGNG...... ......YASF NGTSMATPHV
(BAPB92)  ....AGLDIV APGVNVQSTY PGST...... ......YASL NGTSMATPHV
(BSSDY)   ....AELEVM APGVSVYSTY PSNT...... ......YTSL NGTSMASPHV
(TVTHER)  ....SVVDVA APGSWIYSTY PTST...... ......YASL SGTSMATPHV
(BLSAVI)  ....AGLDIV APGVNVQSTY PGST...... ......YASL NGTSMATPHV
(BSISP1)  ....KEIDLV APGENILSTL PNKK...... ......YGKL TGTSMAAPHV
(BSEPR)   ....DEVEFS APGTNITSTY LNQY...... ......YATG SGTSQATPHA
(JP170)   RDGRIKPDVM APGTYILSAR SSLAPDSSFW ANHDSKYAYM GGTSMATPIV 230        240        250        260
             |          |          |          |
(BASBPN)  AGAAALILSK HP.....NWT NTQVRSSLEN TTTKLGDSF. ..YYGKGLIN
(BLS147)  AGVAALVKSR YP.....SYT NNQIRQRINQ TATYLGSPS. ..LYGNGLVH
(BYSYAB)  AGVAALVKQK NP.....SWS NVQIRNHLKN TATNLGNTT. ..QFGSGLVN
(BAPB92)  AGAAALVKQK NP.....SWS NVQIRNHLKN TATSLGSTN. ..LYGSGLVN
(BSSDY)   AGAAALILSK YP.....TLS ASQVRNRLSS TATNLGDSF. ..YYGKGLIN
(TVTHER)  AGVAGLLASQ .......GRS ASNIRAAIEN TADKISGTG. .TYWAKGRVN
(BLSAVI)  AGAAALVKQK NP.....SWS NVQIRNHLKN TATSLGSTN. ..LYGSGLVN
(BSISP1)  SGALALIKSY EEESFQRKLS ESEVFAQLIR RTLPLDIAKT ..LAGNGFLY
(BSEPR)   AAMFALLKQR DP.....AET NVQLREEMRK NIVDLGTAGR DQQFGYGLIQ
(JP170)   AGNVAQLREH FVKNRGVTPK PSLLKAALIA GAADVGLGFP NGNQGWGRVT

270
             |
(BASBPN)  VQAAAQ.
(BLS147)  AGRATQ.
(BYSYAB)  AEAATR.
(BAPB92)  AEAATR.
(BSSDY)   VEAAAQ.
(TVTHER)  AYKAVQY
(BLSAVI)  AEAATR.
(BSISP1)  LTAPDEL
(BSEPR)   YKAQATD
(JP170)   LDKSLNV
```

Fig. 1 (continued)

PROTEASE VARIANTS AND COMPOSITIONS

CROSS-REFERENCE TO RELATED APPLICATIONS

This application is a continuation of PCT/DK98/00360 filed on Aug. 19, 1998 and claims priority under 35 U.S.C. 119 of Danish application PA 1997 00987 filed on Aug. 29, 1997, the contents of which are fully incorporated herein by reference.

TECHNICAL FIELD

This invention relates to novel mutant protease enzymes or enzyme variants useful in formulating detergent compositions and exhibiting improved wash performance in detergents; cleaning and detergent compositions containing said enzymes; mutated genes coding for the expression of said enzymes when inserted into a suitable host cell or organism; and such host cells transformed therewith and capable of expressing said enzyme variants.

BACKGROUND OF THE INVENTION

In the detergent industry enzymes have for more than 30 years been implemented in washing formulations. Enzymes used in such formulations comprise proteases, lipases, amylases, cellulases, as well as other enzymes, or mixtures thereof. Commercially most important enzymes are proteases.

An increasing number of commercially used proteases are protein engineered variants of naturally occurring wild type proteases, e.g. DURAZYM® (Novo Nordisk A/S), RELASE® (Novo Nordisk A/S), MAXAPEM® (Gist-Brocades N.V.), PURAFECT® (Genencor International, Inc.).

Further a number of protease variants are describe in the art, such as in EP 130756 (GENENTECH) (corresponding to U.S. Resissue Pat. No. 34,606 (GENENCOR)); EP 214435 (HENKEL); WO 87/04461 (AMGEN); WO 87/05050 (GENEX); EP 260105 (GENENCOR); Thomas, Russell, and Fersht (1985) Nature 318 375–376; Thomas, Russell, and Fersht (1987) J. Mol. Biol. 193 803–813; Russel and Fersht Nature 328 496–500 (1987); WO 88/08028 (Genex); WO 88/08033 (Amgen); WO 95/27049 (SOLVAY S.A.); WO 95/30011 (PROCTER & GAMBLE COMPANY); WO 95/30010 (PROCTER & GAMBLE COMPANY); WO 95/29979 (PROCTER & GAMBLE COMPANY); U.S. Pat. No. 5,543,302 (SOLVAY S.A.); EP 251 446 (GENENCOR); WO 89/06279 (NOVO NORDISK A/S); WO 91/00345 (NOVO NORDISK A/S); EP 525 610 A1 (SOLVAY); WO 94/02618 (GIST-BROCADES N.V.); and WO 96/34946 (NOVO NORDISK A/S).

However, even though a number of useful protease variants have been described, there is still a need for new improved protease variants for a number of industrial uses.

Therefore, an object of the present invention, is to provide improved protein engineered protease variants, especially for use in the detergent industry.

SUMMARY OF THE INVENTION

The present inventors have intensively studied numerous of the possible combinations of the T134 and Q137 residues of SAVINASE®, and identified a number of variants with increased improved wash performance.

For further details reference is made to working examples herein (vide infra).

Accordingly, the present invention relates in its first aspect to a subtilase protease variant having improved wash performance in detergents, comprising modification(s) in position(s) 134 and/or 137.

Preferably a subtilase variant according to the invention comprises modifications in position 137, and more preferred comprises modifications in both position 134 and 137.

In a second aspect the invention relates to a subtilase enzyme variant having improved wash performance in detergents, comprising at least one modification chosen from the group comprising:

134A+137L
134S+137L
134A+137E
137F
137L
134V+137T
134V+137L
134C+137S
134A+137C
137C
137D; or a variant comprising one or more conservative modification(s) in any of the above mentioned variants (e.g. a conservative modification of a 134A(small a.a.)+137L variant include variants such as 134G(small a.a.)+137L, 134S(small a.a.)+137L, 134T(small a.a.)+137L, and 134M (small a.a.)+137L).

In a third aspect the invention relates to an isolated DNA sequence encoding a subtilase variant of the invention.

In a fourth aspect the invention relates to an expression vector comprising an isolated DNA sequence encoding a subtilase variant of the invention.

In a fifth aspect the invention relates to a microbial host cell transformed with an expression vector according to the fourth aspect.

In a further aspect the invention relates to the production of the subtilisin enzymes of the invention by inserting an expression vector according to the fourth aspect into a suitable microbial host, cultivating the host to express the desired subtilase enzyme, and recovering the enzyme product.

Even further the invention relates to a composition comprising a subtilase variant of the invention.

Finally the invention relates to the use of the mutant enzymes for a number of industrial relevant uses, in particular for use in cleaning compositions and cleaning compositions comprising the mutant enzymes, especially detergent compositions comprising the mutant subtilisin enzymes.

Definitions

Prior to discussing this invention in further detail, the following term will first be defined.

ABBREVIATIONS

Nomenclature of Amino Acids

| A | = | Ala | = | Alanine |
| V | = | Val | = | Valine |
| L | = | Leu | = | Leucine |
| I | = | Ile | = | Isoleucine |
| P | = | Pro | = | Proline |

-continued

| ABBREVIATIONS | | | |
|---|---|---|---|
| F | = | Phe | = Phenylalanine |
| W | = | Trp | = Tryptophan |
| M | = | Met | = Methionine |
| G | = | Gly | = Glycine |
| S | = | Ser | = Serine |
| T | = | Thr | = Threonine |
| C | = | Cys | = Cysteine |
| Y | = | Tyr | = Tyrosine |
| N | = | Asn | = Asparagine |
| Q | = | Gln | = Glutamine |
| D | = | Asp | = Aspartic Acid |
| E | = | Glu | = Glutamic Acid |
| K | = | Lys | = Lysine |
| R | = | Arg | = Arginine |
| H | = | His | = Histidine |
| X | = | Xaa | = Any amino acid |
| Nomenclature of nucleic acids | | | |
| A | = | | Adenine |
| G | = | | Guanine |
| C | = | | Cytosine |
| T | = | | Thymine (only in DNA) |
| U | = | | Uracil (only in RNA) |

Nomenclature of Variants

In describing the various enzyme variants produced or contemplated according to the invention, the following nomenclatures have been adapted for ease of reference:

Original amino acid(s) position(s) substituted amino acid(s)

According to this the substitution of Glutamic acid for glycine in position 195 is designated as:

Gly 195 Glu or G195E a deletion of glycine in the same position is:

Gly 195* or G195* and insertion of an additional amino acid residue such as lysine

Gly 195 GlyLys or G195GK

Where a deletion in comparison with the sequence used for the numbering is indicated, an insertion in such a position is indicated as:

*36 Asp or *36D for insertion of an aspartic acid in position 36

Multiple mutations are separated by pluses, i.e.:

Arg 170 Tyr+Gly 195 Glu or R170Y+G195E representing mutations in positions 170 and 195 substituting tyrosine and glutamic acid for arginine and glycine, respectively.

Proteases

Enzymes cleaving the amide linkages in protein substrates are classified as proteases, or (interchangeably) peptidases (see Walsh, 1979, *Enzymatic Reaction Mechanisms*. W. H. Freeman and Company, San Francisco, Chapter 3).

Numbering of Amino Acid Positions/residues

If no other mentioned the amino acid numbering used herein correspond to that of the subtilase BPN (BASBPN) sequence. For further description of the BPN sequence see Siezen et al., *Protein Engng.* 4 (1991) 719–737 and FIG. 1.

Serine Proteases

A serine protease is an enzyme which catalyzes the hydrolysis of peptide bonds, and in which there is an essential serine residue at the active site (White, Handler and Smith, 1973 *"Principles of Biochemistry,"* Fifth Edition, McGraw-Hill Book Company, NY, pp. 271–272).

The bacterial serine proteases have molecular weights in the 20,000 to 45,000 Daltons range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) *Bacteriological Rev.* 41 711–753).

Subtilases

A sub-group of the serine proteases tentatively designated subtilases has been proposed by Siezen et al., *Protein Engng.* 4 (1991) 719–737. They are defined by homology analysis of more than 40 amino acid sequences of serine proteases previously referred to as subtilisin-like proteases. A subtilisin was previously defined as a serine protease produced by Gram-positive bacteria or fungi, and according to Siezen et al. now is a subgroup of the subtilases. A wide variety of subtilases have been identified, and the amino acid sequence of a number of subtilases have been determined. For a more detailed description of such subtilases and their amino acid sequences reference is made to Siezen et al. and FIG. 1 herein.

One subgroup of the subtilases, I-S1, comprises the "classical" subtilisins, such as subtilisin 168, subtilisin BPN', subtilisin Carlsberg (ALCALASE®, NOVO NORDISK A/S), and subtilisin DY.

A further subgroup of the subtilases I-S2, is recognised by Siezen et al. (supra). Sub-group I-S2 proteases are described as highly alkaline subtilisins and comprise enzymes such as subtilisin PB92 (MAXACAL®, Gist-Brocades NV), subtilisin 309 (SAVINASE®, NOVO NORDISK A/S), subtilisin 147 (ESPERASE®, NOVO NORDISK A/S), and alkaline elastase YaB.

"SAVINASE®"

SAVINASE® is marketed by NOVO NORDISK A/S.

It is subtilisin 309 from *B. Lentus* and differs from BABP92 only in having N87S (see FIG. 1 herein).

Parent Subtilase

The term "parent subtilase" is a subtilase defined according to Siezen et al. (Protein Engineering 4:719–737 (1991)). For further details see description of "SUBTILASES" immediately above. A parent subtilase may also be a subtilase isolated from a natural source, wherein subsequent modification have been made while retaining the characteristic of a subtilase.

Alternatively the term "parent subtilase" may be termed "wild-type subtilase".

Modification(s) of a Subtilase Variant

The term "modification(s)" used in connection with modification(s) of a subtilase variant as discussed herein is defined to include chemical modification as well as genetic manipulation. The modification(s) can be by substitution, deletion and/or insertions in or at the amino acid(s) of interest.

Subtilase Variant

In the context of this invention, the term subtilase variant or mutated subtilase means a subtilase that has been produced by an organism which is expressing a mutant gene derived from a parent microorganism which possessed an original or parent gene and which produced a corresponding parent enzyme, the parent gene having been mutated in order to produce the mutant gene from which said mutated subtilase protease is produced when expressed in a suitable host.

Homologous Subtilase Sequences

Specific amino acid residues of SAVINASE® subtilase are identified for modification herein to obtain a subtilase variant of the invention.

However, the invention is not limited to modifications of this particular subtilase, but extend to other parent (wild-type) subtilases, which have a homologous primary structure to that of SAVINASE®.

In order to identify other homologous subtilases, within the scope of this invention, an alignment of said subtilase(s) to a group of previously aligned subtilases is performed keeping the previous alignment constant. A comparison to 18 highly conserved residues in subtilases is performed. The 18 highly conserved residues are shown in table I (see Siezen et al. for further details relating to said conserved residues).

TABLE I 18 highly conserved residues in subtilases

| Position: | Conserved residue |
|---|---|
| 23 | G |
| 32 | D |
| 34 | G |
| 39 | H |
| 64 | H |
| 65 | G |
| 66 | T |
| 70 | G |
| 83 | G |
| 125 | S |
| 127 | G |
| 146 | G |
| 154 | G |
| 155 | N |
| 219 | G |
| 220 | T |
| 221 | S |
| 225 | P |

After aligning allowing for necessary insertions and deletions in order to maintain the alignment suitable homologous residues are identified. Said homologous residues can then be modified according to the invention.

Using the CLUSTALW (version 1.5, April 1995) computer alignment program (Thompson, J. D., Higgins, D. G. and Gibson, T. J. (1994) Nucleic Acids Research, 22:4673–4680.), with GAP open penalty of 10.0 and GAP extension penalty of 0.1, using the BLOSUM30 protein weight matrix, alignment of a given subtilase to a group of previously aligned subtilases is achieved using the Profile alignments option in the program. For a given subtilase to be within the scope of the invention, preferably 100% of the 18 highly conserved residues should be conserved. However, alignment of greater than or equal to 17 out of the 18 residues, or as little as 16 of said conserved residues is also adequate to identify homologous residues. Conservation of the, in subtilases, catalytic triad Asp32/His64/Ser221 should be maintained.

The previously defined alignment is shown FIG. 1, where the percent identity of the individual subtilases in this alignment to the 18 highly conserved residues are shown too.

Based on this description it is routine for a person skilled in the art to identify suitable homologous subtilases and corresponding homologous residues, which can be modified according to the invention. To illustrate this table II below shows a limited list a homologous subtilases and corresponding suitable residues to be modified according to the invention.

TABLE II

Homologous Subtilases and corresponding homologous residues, suitable to be modified according to the invention

| Pos nz. | BASBPN | BYSYAB | BLS309 | BLS147 | TVTHER |
|---|---|---|---|---|---|
| 134 + 137 | A134A + A137L | T134A + Q137L | T134A + Q137L | T134A + L137L | G134A + Q137L |
| 134 + 137 | A134S + A137L | T134S + Q137L | T134S + Q137L | T134S + L137L | G134S + Q137L |
| 137 | A137C | Q137C | Q137C | L137C | Q137C |

It is obvious that a similar or larger table covering other homologous subtilases may easily be produced by a person skilled in the art.

Wash Performance

The ability of an enzyme to catalyze the degradation of various naturally occurring substrates present on the objects to be cleaned during e.g. wash is often referred to as its washing ability, washability, detergency, or wash performance. Throughout this application the term wash performance will be used to encompass this property.

Isolated DNA sequence

The term "isolated", when applied to a DNA sequence molecule, denotes that the DNA sequence has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774–78, 1985). The term "an isolated DNA sequence" may alternatively be termed "a cloned DNA sequence".

Isolated protein

When applied to a protein, the term "isolated" indicates that the protein is found in a condition other than its native environment. In a preferred form, the isolated protein is substantially free of other proteins, particularly other homologous proteins (i.e. "homologous impurities" (see below)). It is preferred to provide the protein in a highly purified form, i.e., greater than 40% pure, greater than 60% pure, greater than 80% pure, more preferably greater than 95% pure, and even more preferably greater than 99% pure, as determined by SDS-PAGE.

The term "isolated protein" may alternatively be termed "purified protein".

Homologous Impurities

The term "homologous impurities" means any impurity (e.g. another polypeptide than the polypeptide of the invention) which originate from the homologous cell where the polypeptide of the invention is originally obtained from.

Obtained from

The term "obtained from" as used herein in connection with a specific microbial source, means that the polynucleotide and/or polypeptide produced by the specific source, or by a cell in which a gene from the source have been inserted.

Substrate

The term "Substrate" used in connection with a substrate for a protease is should be interpreted in its broadest form as comprising a compound containing at least one peptide bond susceptible to hydrolysis by a subtilisin protease.

Product

The term "product" used in connection with a product derived from a protease enzymatic reaction should in the context of this invention be interpreted to include the products of a hydrolysis reaction involving a subtilase protease. A product may be the substrate in a subsequent hydrolysis reaction.

BRIEF DESCRIPTION OF THE FIGURE BRIEF DESCRIPTION OF THE FIGURES

FIG. 1 shows an alignment of a number of homologous subtilases (SEQ ID NOS:1–10), which are aligned to 18 highly conserved residues in subtilases. 18 highly conserved residues are highlighted in bold. All shown subtilases, except JP170, have 100% identity in said conserved residues. JP170 is having an "N" in stead of "G" in conserved residues G146.

DETAILED DESCRIPTION OF THE INVENTION

Subtilase Variants with Improved Wash Performance

The present inventors have identified the improved wash performance variants in BLS309 (SAVINASE®).

Accordingly, an embodiment of the invention relates to a subtilase enzyme variant, wherein the modification is chosen from the group comprising:

T134A+Q137L

T134S+Q137L

T134A+Q137E

Q137F

Q137L

T134V+Q137T

T134V+Q137L

T134C+Q137S

T134A+Q137C

Q137C

Q137D; or a variant comprising one or more conservative modification(s) in any of the above mentioned variants (e.g. a conservative modification of a T134A(small a.a.)+Q137L variant include variants such as T134G(small a.a.)+Q137L, T134S(small a.a.)+Q137L, T134T(small a.a.)+Q137L, and T134M(small a.a.)+Q137L).

Numerous subtilase variants of the invention is tested herein and showing improved wash-performance in detergents (see working examples herein (vide infra)).

It is well known in the art that substitution of one amino acid to a similar conservative amino acid only give a minor change in the characteristic of the enzyme.

Table III below list groups of conservative amino acids.

TABLE III

| Conservative amino acid substitutions | |
|---|---|
| Basic: | arginine |
|  | lysine |
|  | histidine |
| Acidic: | glutamic acid |
|  | aspartic acid |
| Polar: | glutamine |
|  | asparagine |
| Hydrophobic: | leucine |
|  | isoleucine |
|  | valine |

TABLE III-continued

| Conservative amino acid substitutions | |
|---|---|
| Aromatic: | phenylalanine |
|  | tryptophan |
|  | tyrosine |
| Small: | glycine |
|  | alanine |
|  | serine |
|  | threonine |
|  | methionine |

Accordingly, subtilase variants such as 134A+137L, 134G+137L, 134S+137L, 134T+137L, and 134M+137L will have a similar wash-performance improvement. Further, subtilase variants such as T134A+Q137L, T134G+Q137L, T134S+Q137L, T134T+Q137L, and T134M+Q137L will have a similar wash-performance improvement too.

Based on the disclosed subtilase variants herein, it is routine work, for a person skilled in the art, to identify further suitable conservative substitutions in order to obtain a subtilase variant with improved wash-performance.

In embodiments of the invention, the subtilases of interest are those belonging to the subgroups I-S1 and I-S2.

Relating to subgroup I-S1 preferred parent subtilase is chosen from the group comprising ABSS168, BASBPN, BSSDY, and BLSCAR or functional variants thereof having retained the characteristic of sub-group I-S1.

Relating to subgroup I-S2 preferred parent subtilase is chosen from the group comprising BLS147, BLS309, BAPB92, TVTHER AND BYSYAB or functional variants thereof having retained the characteristic of sub-group I-S2.

The present invention also comprises any one or more modifications in the above mentioned positions in combination with any other modification to the amino acid sequence of the parent enzyme. Especially combinations with other modifications known in the art to provide improved properties to the enzyme are envisaged. The art describe a number of subtilase variants with different improved properties and a number of those are mentioned in the "Background of the invention" section herein (vide supra). Those references are disclosed here as references to identify a subtilase variant, which advantageously can be combined with a subtilase variant of the invention.

Such combinations comprise the positions: 222 (improve oxidation stability), 218 (improves thermal stability), substitutions in the Ca-binding sites stabilising the enzyme, e.g. position 76, and many other apparent from the prior art.

In further embodiments a subtilase variant of the invention may advantageously be combined with one or more modification(s) in any of the positions: 27, 36, 57, 76, 97, 101, 104, 120, 123, 167, 170, 206, 218, 222, 224, 235 and 274.

Specifically the following BLS309 and BAPB92 variants are considered appropriate for combination: K27R, *36D, S57P, N76D, G97N, S101G, V104A, V104N, V104Y, H120D, N123S, Y167A, Y167I, R170S, R170L, R170N, Q206E, N218S, M222S, M222A, T224S, K235L and T274A.

Furthermore variants comprising any of the variants V104N+S101G, K27R+V104Y+N123S+T274A, or N76D+V104A or other combinations of these mutations (V104N, S101G, K27R, V104Y, N123S, T274A, N76D, V104A), in combination with any one or more of the modification(s) mentioned above exhibit improved properties.

Even further subtilase variants of the main aspect(s) of the invention are preferably combined with one or more modification(s) in any of the positions 129, 131, 133 and 194, preferably as 129K, 131H, 133P, 133D and 194P modifications, and most preferably as P129K, P131H, A133P, A133D and A194P modifications. Any of those modifications) may give a higher expression level of a subtilase variant of the invention.

Method for Producing Mutations in Subtilase Genes

Many methods for cloning a subtilase of the invention and for introducing mutations into genes (e.g. subtilase genes) are well known in the art.

In general standard procedures for cloning of genes and introducing mutations (random and/or site directed) into said genes may be used in order to obtain a subtilase variant of the invention. For further description of suitable techniques reference is made to working examples herein (vide infra) and (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990); and WO 96/34946.

Expression Vectors

A recombinant expression vector comprising a DNA construct encoding the enzyme of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gen, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cell

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present enzyme and includes bacteria, yeast, fungi and higher eukaryotic cells.

Examples of bacterial host cells which, on cultivation, are capable of producing the enzyme of the invention are gram-positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis,* or strains of Streptomyces, such as *S. lividans* or *S. murinus,* or gram-negative bacteria such as *Echerichia coli.* The transformation of the bacteria may be effected by protoplast transformation, electroporation, conjugation, or by using competent cells in a manner known per se (cf. Sambrook et al., supra).

When expressing the enzyme in bacteria such as *E. coli,* the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as Bacillus or Streptomyces strains, the enzyme may be retained in the cytoplasm, or may be directed to the extracellular medium by a bacterial secretion sequence. In the latter case, the enzyme may be recovered from the medium as described below.

Method of Producing Subtilase

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention.

Thereby it is possible to make a highly purified subtilase composition, characterized in being free from homologous impurities.

In this context homologous impurities means any impurities (e.g. other polypeptides than the enzyme of the invention) which originate from the homologous cell where the enzyme of the invention is originally obtained from.

The medium used to culture the transformed host cells may be any conventional medium suitable for growing the host cells in question. The expressed subtilase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Use of a Subtilase Variant of the Invention

A subtilase protease variant of the invention may be used for a number of industrial applications, in particular within the detergent industry.

Further the invention relates to an enzyme composition, which comprise a subtilase variant of the invention.

An summary of preferred industrial applications and corresponding preferred enzyme compositions are described below.

This summary is not in any way intended to be a complete list of suitable applications of a subtilase variant of the invention. A subtilase variants of the invention may be used in other industrial applications known in the art to include use of a protease, in particular a subtilase.

Detergent Compositions Comprising the Mutant Enzymes

The present invention comprises the use of the mutant enzymes of the invention in cleaning and detergent compositions and such compositions comprising the mutant subtilisin enzymes. Such cleaning and detergent compositions are well described in the art and reference is made to WO 96/34946; WO 97/07202; WO 95/30011 for further description of suitable cleaning and detergent compositions.

Further reference is made to workings example(s) herein showing wash performance improvements for a number of subtilase variants of the invention.

Detergent Disclosure and Examples

Surfactant System

The detergent compositions according to the present invention comprise a surfactant system, wherein the surfactant can be selected from nonionic and/or anionic and/or cationic and/or ampholytic and/or zwitterionic and/or semipolar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present inven-tion comprise as a surfactant one or more of the nonionic and/or anionic surfactants described herein.

Polyethylene, polypropylene, and polybutylene oxide condensates of alkyl phenols are suitable for use as the nonionic surfactant of the surfactant systems of the present inven-tion, with the polyethylene oxide condensates being pre-ferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of the surfactant systems of the present invention are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula $$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, pre-ferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula

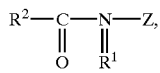

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulfate surfactants. Examples hereof are water soluble salts or acids of the formula $RO(A)_mSO3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydro-xyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}$E(1.0)M), $C_{12}$–$C_{18}$ alkyl polyethoxylate (2.25) sulfate ($C_{12}$–$C_{18}$(2.25)M, and $C_{12}$–$C_{18}$ alkyl polyethoxylate (3.0) sulfate ($C_{12}$–$C_{18}$E(3.0)M), and $C_{12}$–$C_{18}$ alkyl polyethoxylate (4.0) sulfate ($C_{12}$–$C_{18}$E(4.0)M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

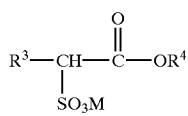

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16}$–$C_{18}$ alkyl chains are preferred for higher wash temperatures (e.g. above about 50° C.).

Other anionic surfactants useful for detersive purposes can also be included in the laundry detergent compositions of the present invention. Theses can include salts (including, for example, sodium, potassium, ammonium, and substituted ammonium salts such as mono- di- and triethanolamine salts) of soap, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$—M+ wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulfonates are highly preferred. Especially preferred are linear (straight-chain) alkyl benzene sulfonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1 to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

$$[R^2(OR^3)_y][R^4(OR^3)_y]_2R^5N+X-$$

wherein $R^2$ is an alkyl or alkyl benzyl group having from about 8 to about 18 carbon atoms in the alkyl chain, each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula:

$$R_1R_2R_3R_4N^+X^- \qquad (i)$$

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{40})_x$H where x has a value from 2 to 5, and X is an anion. Not more than one of $R_2$, $R_3$ or $R_4$ should be benzyl.

The preferred alkyl chain length for $R_1$ is $C_{12}$–$C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:

coconut trimethyl ammonium chloride or bromide;

coconut methyl dihydroxyethyl ammonium chloride or bromide;

decyl triethyl ammonium chloride;

decyl dimethyl hydroxyethyl ammonium chloride or bromide;

$C_{12}$–$C_{15}$ dimethyl hydroxyethyl ammonium chloride or bromide;

coconut dimethyl hydroxyethyl ammonium chloride or bromide;

myristyl trimethyl ammonium methyl sulphate;

lauryl dimethyl benzyl ammonium chloride or bromide;

lauryl dimethyl (ethenoxy)$_4$ ammonium chloride or bromide;

choline esters (compounds of formula (i) wherein $R_1$ is $$CH_2-CH_2-O-\underset{O}{\underset{\|}{C}}-C_{12-14} \text{ alkyl and } R_2R_3R_4 \text{ are methyl}).$$

di-alkyl imidazolines [compounds of formula (i)].

Other cationic surfactants useful herein are also described in U.S. Pat. No. 4,228,044 and in EP 000 224.

When included therein, the laundry detergent compositions of the present invention typically comprise from. 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula:

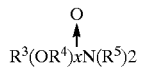

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Builder System

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686, and 2,446,487, U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2,-ethane tetracarboxylates, 1,1,3,3-propane tetracarboxylates containing sulfo substituents include the sulfosuccinate derivatives disclosed in British Patent Nos. 1,398, 421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadien-ide pentacarboxylates, 2,3,4,5-tetrahydro-furan-cis, cis, cis-tetracarboxylates, 2,5-tetrahydro-furan-cis, discarboxylates, 2,2,5,5,-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine- N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the enzyme preparation of the invention, comprise other enzyme(s) which provides cleaning performance and/or fabric care benefits.

Such enzymes include other proteases, lipases, cutinases, amylases, cellulases, peroxidases, oxidases (e.g. laccases).

Proteases: Any other protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Preferred commercially available protease enzymes include those sold under the trade names Alcalase, Savinase, Primase, Durazym, and Esperase by Novo Nordisk A/S (Denmark), those sold under the tradename Maxatase, Maxacal, Maxapem, Properase, Purafect and Purafect OXP by Genencor International, and those sold under the tradename opticlean and Optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases: Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a Pseudomonas lipase such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, a *P. fluorescens* lipase, a Bacillus lipase, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani pisi* (e.g. described in WO 90/09446).

Especially suitable lipases are lipases such as M1 Lipase™, Luma fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases: Any amylase ($\alpha$ and/or $\beta$) suitable for use in alkaline solutions can be used. Suitable amylases include those of bacterial or fungal origin. Chemically or genetically modified mutants are included. Amylases include, for example, $\alpha$-amylases obtained from a special strain of *B. licheniformis,* described in more detail in GB 1,296, 839. Commercially available amylases are Duramyl™, Termamyl™, Fungamyl™ and BAN™ (available from Novo Nordisk A/S) and Rapidase™ and Maxamyl P™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases: Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307, which discloses fungal cellulases produced from *Humicola insolens.* Especially suitable cellulases are the cellulases having colour care benefits. Examples of such cellulases are cellulases described in European patent application No. 0 495 257.

Commercially available cellulases include Celluzyme™ produced by a strain of *Humicola insolens,* (Novo Nordisk A/S), and KAC-500(B)™ (Kao Corporation).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases: Peroxidase enzymes are used in combination with hydrogen peroxide or a source thereof (e.g. a percarbonate, perborate or persulfate). Oxidase enzymes are used in combination with oxygen. Both types of enzymes are used for "solution bleaching", i.e. to prevent transfer of a textile dye from a dyed fabric to another fabric when said fabrics are washed together in a wash liquor, preferably together with an enhancing agent as described in e.g. WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching agents: Additional optional detergent ingredients that can be included in the detergent compositions of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. Nos. 4,483,781, 740,446, EP 0 133 354 and U.S Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Ser. No. 08/136,626.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc and/or aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Bleaching agents may also comprise a manganese catalyst. The manganese catalyst may, e.g., be one of the compounds described in "Efficient manganese catalysts for low-temperature bleaching", *Nature* 369, 1994, pp. 637–639.

Suds suppressors: Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or waterdispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxane-glycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Application EP 0 593 841.

Especially preferred silicone suds controlling agents are described in European Patent Application No. 92201649.8. Said compositions can comprise a silicone/silica mixture in combination with fumed nonporous silica such as Aerosil$^R$.

The suds suppressors described above are normally employed at levels of from 0.001% to 2% by weight of the composition, preferably from 0.01% to 1% by weight.

Other components: Other components used in detergent compositions may be employed such as soil-suspending agents, soil-releasing agents, optical brighteners, abrasives, bactericides, tarnish inhibitors, coloring agents, and/or encapsulated or nonencapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2' disulphonate, disodium 4,-4'-bis-(2-morpholino-4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4',4"-bis-(2,4-dianilino-s-tri-azin-6 ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2,1,3-triazol-2-yl)-stilbene-2,2' disulphonate, di-so-dium 4,4'bis(2-anilino-4-(1-methyl-2-hydroxyethylamino)-s-triazin-6-ylami-no)stilbene-2,2'disulphonate, sodium 2(stilbyl-4"-(naphtho-1',2':4,5)-1,2,3,-triazole-2"-sulphonate and 4,4"-bis(2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

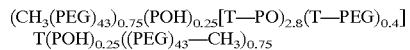

where PEG is —(OC$_2$H$_4$)O—, PO is (OC$_3$H$_6$O) and T is (POOC$_6$H$_4$CO).

Also very useful are modified polyesters as random copolymers of dimethyl terephthalate, dimethyl sulfoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulfoisophthalic acid, and have a molecular weight of about 3.000. The polyesters and their method of preparation are described in detail in EP 311 342.

Softening agents: Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono C$_{12}$–C$_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric dye-transfer inhibiting agents: The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of—waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention.

In the detergent compositions, the abbreviated component identifications have the following meanings:

LAS: Sodium linear $C_{12}$ alkyl benzene sulphonate
TAS: Sodium tallow alkyl sulphate
XYAS: Sodium $C_{1X}$—$C_{1Y}$ alkyl sulfate
SS: soap surfactant of formula 2-butyl octanoic acid
25EY: A $C_{12}$—$C_{15}$ predominantly linear primary alcohol condensed with an average of Y moles of ethylene oxide
45EY: A $C_{14}$—$C_{15}$ predominantly linear primary alcohol condensed with an average of Y moles of ethylene oxide
XYEZS: $C_{1X}$—$C_{1Y}$ sodium alkyl sulfate condensed with an average of Z moles of ethylene oxide per mole
Nonionic: $C_{13}$—$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh
CFAA: $C_{12}$—$C_{14}$ alkyl N-methyl glucamide
TFAA: $C_{16}$—$C_{18}$ alkyl N-methyl glucamide
Silicate: Amorphous Sodium Silicate ($SiO_2$:$Na_2O$ ratio = 2.0)
NaSKS-6: Crystalline layered silicate of formula $\delta$-$Na_2Si_2O_5$
Carbonate: Anhydrous sodium carbonate
Phosphate: Sodium tripolyphosphate
MA/AA: Copolymer of 1:4 maleic/acrylic acid, average molecular weight about 80,000
Polyacrylate: Polyacrylate homopolymer with an average molecular weight of 8,000 sold under the tradename PA30 by BASF Gmbh
Zeolite A: Hydrated Sodium Aluminosilicate of formula $Na_{12}(AlO_2SiO_2)_{12}$ . $27H_2O$ having a primary particle size in the range from 1 to 10 micrometers
Citrate: Tri-sodium citrate dihydrate
Citric: Citric Acid
Perborate: Anhydrous sodium perborate monohydrate bleach, empirical formula $NaBO_2$ . $H_2O_2$
PB4: Anhydrous sodium perborate tetrahydrate
Percarbonate: Anhydrous sodium percarbonate bleach of empirical formula $2Na_2CO_3$ . $3H_2O_2$
TAED: Tetraacetyl ethylene diamine
CMC: Sodium carboxymethyl cellulose
DETPMP: Diethylene triamine penta (methylene phosphonic acid), marketed by Monsanto under the Tradename Dequest 2060
PVP: Polyvinylpyrrolidone polymer
EDDS: Ethylenediamine-N, N'-disuccinic acid, [S,S] isomer in the form of the sodium salt
Suds 25% paraffin wax Mpt 50° C., 17% hydrophobic silica, 58% Suppressor: paraffin oil
Granular Suds 12% Silicone/silica, 18% stearyl alcohol, 70% suppressor: starch in granular form
Sulphate: Anhydrous sodium sulphate
HMWPEO: High molecular weight polyethylene oxide
TAE 25: Tallow alcohol ethoxylate (25)

Detergent Example I

A granular fabric cleaning composition in accordance with the invention may be prepared as follows:

| | |
|---|---|
| Sodium linear $C_{12}$ alkyl benzene sulfonate | 6.5 |
| Sodium sulfate | 15.0 |
| Zeolite A | 26.0 |
| Sodium nitrilotriacetate | 5.0 |
| Enzyme of the invention | 0.1 |
| PVP | 0.5 |
| TAED | 3.0 |

| | |
|---|---|
| Boric acid | 4.0 |
| Perborate | 18.0 |
| Phenol sulphonate | 0.1 |
| Minors | Up to 100 |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinylimidazole and vinylpyrrolidone | — | 0.2 |
| Perborate | 1.0 | — |
| Phenol sulfonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

| | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

Leather Industry Applications

A subtilase of the invention may be used in the leather industry, in particular for use in depilation of skins.

In said application a subtilase variant of the invention is preferably used in an enzyme composition which further comprise another protease.

For a more detailed description of suitable other proteases see section relating to suitable enzymes for use in a detergent composition (vide supra).

Wool Industry Applications

A subtilase of the invention may be used in the wool industry, in particular for use in cleaning of clothes comprising wool.

In said application a subtilase variant of the invention is preferably used in an enzyme composition which further comprise another protease.

For a more detailed description of suitable other proteases see section relating to suitable enzymes for use in a detergent composition (vide supra).

The invention is described in further detail in the following examples which are not in any way intended to limit the scope of the invention as claimed.

Materials and Methods

Strains

B. subtilis DN1885 (Diderichsen et al., 1990).

B. lentus 309 and 147 are specific strains of Bacillus lentus, deposited with the NCIB and accorded the accession numbers NCIB 10309 and 10147, and described in U.S. Pat. No. 3,723,250 incorporated by reference herein.

E. coli MC 1000 (M. J. Casadaban and S. N. Cohen (1980); J. Mol. Biol. 138 179–207), was made r⁻,m⁺ by conventional methods and is also described in U.S. patent application Ser. No. 039,298.

Plasmids pJS3: E. coli-B. subtilis shuttle vector containing a synthetic gene encoding for subtilase 309. (Described by Jacob Schiødt et al. in Protein and Peptide letters 3:39–44 (1996)).

pSX222: B. subtilis expression vector (Described in WO 96/34946).

General Molecular Biology Methods

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

Enzymes for DNA Manipulations

Unless otherwise mentioned all enzymes for DNA manipulations, such as e.g. restriction endonucleases, ligases etc., are obtained from New England Biolabs, Inc.

Proteolytic Activity

In the context of this invention proteolytic activity is expressed in Kilo NOVO Protease Units (KNPU). The activity is determined relatively to an enzyme standard (SAVINASEÔ), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novo Nordisk A/S, Denmark, which folder is hereby included by reference.

A GU is a Glycine Unit, defined as the proteolytic enzyme activity which, under standard conditions, during a 15-minutes' incubation at 40 deg C., with N-acetyl casein as substrate, produces an amount of $NH_2$-group equivalent to 1 mmole of glycine.

Enzyme activity can also be measured using the PNA assay, according to reaction with the soluble substrate succinyl-alanine-alanine-proline-phenyl-alanine-para-nitrophenol, which is described in the Journal of American Oil Chemists Society, Rothgeb, T. M., Goodlander, B. D., Garrison, P. H., and Smith, L. A., (1988).

Fermentation

Fermentation of subtilase enzymes were performed at 300° C. on a rotary shaking table (300 r.p.m.) in 500 ml baffled Erlenmeyer flasks containing 100 ml BPX medium for 5 days.

Consequently in order to make an e.g 2 liter broth 20 Erlenmeyer flasks were fermented simultaneously.

| Media: |  |
|---|---|
| BPX: Composition (per liter) |  |
| Potato starch | 100 g |
| Ground barley | 50 g |
| Soybean flour | 20 g |
| $Na_2HPO_4$ X 12 $H_2O$ | 9 g |
| Pluronic | 0.1 g |
| Sodium caseinate | 10 g |

The starch in the medium is liquified with α-amylase and the medium is sterilized by heating at 120° C. for 45 minutes. After sterilization the pH of the medium is adjusted to 9 by addition of $NaHCO_3$ to 0.1 M.

EXAMPLES

Example 1

Construction and Expression of Enzyme Variants:Construction and Expression of Enzyme Variants:Construction and Expression of Enzyme Variants:Construction and Expression of Enzyme Variants:Construction and Expression of Enzyme Variants:Construction and Expression of Enzyme Variants Site-directed mutagenesis:

Subtilase 309 site-directed variants was made by the "Unique site elimination (USE)" or the "Uracil-USE" technique described respectively by Deng et al. (Anal. Biochem. 200:81–88 (1992)) and Markvardsen et al. (BioTechniques 18(3):371–372 (1995)).

The template plasmid was pJS3, or a analogue of this containing a variant of Subtilase 309, e.g. USE mutagenesis was performed on pJS3 analogue containing a gene encoding the T134A variant with a oligonucleotide directed to the construct Q137L variant resulting in a final T134A+Q137L Subtilase 309 variant.

The in pJS3 constructed Subtilase 309 variants was then subcloned into the B.subtilis pSX222 expression plasmid, using the restriction enzymes KpnI and MluI.

Localized Random mutagenesis:

The overall strategy to used to perform localized random mutagenesis was:

a mutagenic primer (oligonucleotide) was synthesized which corresponds to the part of the DNA sequence to be mutagenized except for the nucleotide(s) corresponding to amino acid codon(s) to be mutagenized.

Subsequently, the resulting mutagenic primer was used in a PCR reaction with a suitable opposite primer. The resulting PCR fragment was purified and digested and cloned into a E.coli-B.subtilis shuttle vector.

Alternatively and if necessary, the resulting PCR fragment is used in a second PCR reaction as a primer with a second suitable opposite primer so as to allow digestion and cloning of the mutagenized region into the shuttle vector. The PCR reactions are performed under normal conditions.

Following this strategy a localized random library was constructed in SAVINASE wherein both position T134 and Q137 was completely randomized.

One oligonucleotide was synthesized with 25% of each of the four bases (N) in the first and the second base at amino acid codons wanted to be mutagenized. The third nucleotide (the wobble base) in codons were synthesized with 50%G/50%C (S) to avoid two (TAA, TGA) of the three stop-codons.

The mutagenic primer (5'-G AAC GCC TCT AGA AGT CGC GCT ATT AAC AGC SNN CTC GAG SNN GGC ACT TGG CGA AGG GCT TCC-3' (anti-sense (SEQ ID NO: 11)) were used in a PCR reaction with a suitab opposite primer (e.g. 5' GAA CTC GAT CCA GCG ATT TC 3' (sense)(SEQ ID NO:12)) and the plasmid pJS3 as template. This resulting PCR product was cloned into the pJS3 shuttle vector by using the restriction enzymes HindIII and XbaI.

The in pJS3 constructed localized random library was then subcloned into the B.subtilis pSX222 expression plasmid, using the restriction enzymes KpnI and MluI.

The library prepared contained approximately 100,000 individual clones/library.

Ten randomly chosen colonies were sequenced to confirm the mutations designed.

In order to purify a subtilase variant of the invention the B.subtilis pSX222 expression plasmid comprising a variant of the invention was transformed into a competent B. subtilis strain and was fermented as described above in a medium containing 10 µg/ml Chloramphenicol (CAM).

EXAMPLE 2
Purification of Enzyme Variants: Purification of Enzyme Variants:Purification of Enzyme Variants:Purification of Enzyme Variants:Purification of Enzyme Variants:Purification of Enzyme Variants This procedure relates to purification of a 2 liter scale fermentation of the Subtilisin 147 enzyme, the Subtilisin 309 enzyme or mutants thereof.

Approximately 1.6 liters of fermentation broth were centrifuged at 5000 rpm for 35 minutes in 1 liter beakers. The supernatants were adjusted to pH 6.5 using 10% acetic acid and filtered on Seitz Supra S100 filter plates.

The filtrates were concentrated to approximately 400 ml using an Amicon CH2A UF unit equipped with an Amicon S1Y10 UF cartridge. The UF concentrate was centrifuged and filtered prior to absorption at room temperature on a Bacitracin affinity column at pH 7. The protease was eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step were combined and applied to a 750 ml Sephadex G25 column (5 cm dia.) equilibrated with a buffer containing 0.01 dimethylglutaric acid, 0.2 M boric acid and 0.002 m calcium chloride adjusted to pH 6.5.

Fractions with proteolytic activity from the Sephadex G25 column were combined and applied to a 150 ml CM Sepharose CL 6B cation exchange column (5 cm dia.) equilibrated with a buffer containing 0.01 M dimethylglutaric acid, 0.2 M boric acid, and 0.002 M calcium chloride adjusted to pH 6.5.

The protease was eluted using a linear gradient of 0–0.1 M sodium chloride in 2 liters of the same buffer (0–0.2 M sodium chloride in case of Subtilisin 147).

In a final purification step protease containing fractions from the CM Sepharose column were combined and concentrated in an Amicon ultrafiltration cell equipped with a GR81PP membrane (from the Danish Sugar Factories Inc.).

By using the techniques of Example 1 for the construction and the above isolation procedure the following subtilisin 309 variants were produced and isolated:

T134A+Q137L
T134S+Q137L
T134A+Q137E
Q137F
Q137L
T134V+Q137T
T134V+Q137L
T134C+Q137S
T134A+Q137C
Q137C; and
Q137D.

EXAMPLE 3
Wash Performance of Detergent Compositions Comprising Enzyme VariantsWash Performance of Detergent Compositions Comprising Enzyme VariantsWash Performance of Detergent Compositions Comprising Enzyme VariantsWash Performance of Detergent Compositions Comprising Enzyme VariantsWash Performance of Detergent Compositions Comprising Enzyme VariantsWash Performance of Detergent Compositions Comprising Enzyme Variants The following examples provide results from a number of washing tests that were conducted under the conditions indicated Experimental Conditions

TABLE IV

Experimental conditions for evaluation of Subtilisin 309 variants.

| Detergent | Protease Model Detergent 95 |
| --- | --- |
| Detergent dose | 3.0 g/l |
| pH | 10.5 |
| Wash time | 10 min. |
| Temperature | 15° C. |
| Water hardness | 6°dH |
| Enzymes | Subtilisin 309 variants as listed below |
| Enzyme conc. | 10 nM |
| Test system | 150 ml glass beakers with a stirring rod |
| Textile/volume | 5 textile pieces (Ø 2.5 cm) in 50 ml detergent |
| Test material | EMPA117 from Center for Testmaterials, Holland |

The detergent used is a simple model formulation. pH is adjusted to 10.5 which is within the normal range for a powder detergent. The composition of model detergent 95 is as follows:

| | |
| --- | --- |
| 25% | STP ($Na_5P_3O_{10}$) |
| 25% | $Na_2SO_4$ |
| 10% | $Na_2CO_3$ |
| 20% | LAS (Nansa 80S) |
| 5.0% | Nonionic tenside (Dobanol 25-7) |
| 5.0% | $Na_2Si_2O_5$ |
| 0.5% | Carboxymethylcellulose (CMC) |
| 9.5% | Water |

Water hardness was adjusted by adding $CaCl_2$ and $MgCl_2$ ($Ca^{2+}:Mg^{2+}=2:1$) to deionized water (see also Surfactants in Consumer Products—Theory, Technology and Application, Springer Verlag 1986). pH of the detergent solution was adjusted to pH 10.5 by addition of HCl.

Measurement of reflectance (R) on the test material was done at 460 nm using a Macbeth ColorEye 7000 photometer (Macbeth, Division of Kollmorgen Instruments Corporation, Germany). The measurements were done according to the manufacturers protocol.

The wash performance of the Subtilisin 309 variants was evaluated by calculating a performance factor:

$$P = \frac{R_{Variant} - R_{Blank}}{R_{Savinase} - R_{Blank}}$$

P: Performance factor $R_{Variant}$: Reflectance of test material washed with variant $R_{Savinase}$: Reflectance of test material washed with Savinase®

$R_{Blank}$: Reflectance of test material washed with no enzyme

The claimed Subtilisin 309 variants all have improved wash performance compared to Savinase®—i.e. P>1.

The variants are divided into improvement classes designated with capital letters:

Class A: $1 < P \leq 1.5$

Class B: $1.5 < P \leq 2$

Class C: $P > 2$

TABLE V

Subtilisin 309 variants and improvement classes.

| Improvement class | Variants |
|---|---|
| A | T134A + Q137L |
|   | T134S + Q137L |
|   | T134A + Q137E |
|   | Q137F |
|   | Q137L |
|   | T134V + Q137T |
|   | T134V + Q137L |
|   | T134C + Q137S |
|   | T134A + Q137C |
|   | Q137C |
|   | Q137D |
| B |   |
| C |   |

What is claimed is:

1. A modified subtilase, comprising a mutation in an amino acid sequence of a subtilase, wherein the mutation is selected from the group consisting of:
   134A+137L,
   134S+137L,
   134A+137E,
   137F,
   134V+137T,
   134V+137L,
   134C+137S,
   134A+137C,
   137C, and
   137D, numbered according to the amino acid sequence of the mature subtilisin BPN'.

2. The modified subtlase of claim 1, wherein the mutation is selected from the group consisting of:

T134A+Q137L,

T134S+Q137L,

T134A+Q137E,

Q137F,

T134V+Q137T,

T134V+Q137L,

T134C+Q137S,

T134A+Q137C,

Q137C, and

Q137D.

3. The modified subtilase of claim 1, comprising at least one further mutation at one or more other positions.

4. The modified subtilase of claim 3, wherein the one or more positions are selected from the group consisting of 27, 36, 57, 76, 97, 101, 104, 120, 123, 167, 170, 206, 218, 222, 224, 235 and 274.

5. The modified subtilase of claim 4, wherein the at least one further mutation is selected from the group consisting of K27R, 36D, S57P, N76D, G97N, S101G, V104A, V104N, V104Y, H120D, N123S, Y167A, Y167I, R170S, R170L, R170N, Q206E, N218S, M222S, M222A, T224S, K235L, and T274A.

6. The modified subtilase of claim 5, wherein the at least one further mutation is selected from the group consisting of V104N+S101G, K27R+V104Y+N123S+T274A, or N76D+V104A, and other combinations of the mutations K27R, N76D, S101G, V104A, V104N, V104Y, N123S, and T274A.

7. The modified subtilase of claim 3, wherein the one or more positions are selected from the group consisting of 129, 131, 133 and 194.

8. The modified subtilase of claim 7, wherein the at least one further mutation is selected from the group consisting of P129K, P131H, A133D, A133P, and A194P.

9. The modified subtilase of claim 1, wherein the subtilase is a subgroup I-S1 subtilase.

10. The modified subtilase of claim 9, wherein the subtilase is selected from the group consisting of subtilisin I168, subtilisin BPN', subtilisin DY, and subtilisin Carlsberg.

11. The modified subtilase of claim 1, wherein the subtilase is a sub-group I-S2 subtilase.

12. The modified subtilase of claim 11, wherein the subtilase is selected from the group consisting of subtilisin 147, subtilisin 309, subtilisin PB92, and subtilisin YaB.

13. A composition comprising a modified subtilase of claim 1, and a surfactant.

14. The composition of claim 13, which additionally comprises an amylase, cellulase, cutinase, lipase, oxidoreductase, or another protease.

15. An isolated DNA sequence encoding a modified subtilase of claim 1.

16. An expression vector comprising an Isolated DNA sequence of claim 15.

17. A microbial host cell transformed with an expression vector of claim 16.

18. The microbial host cell of claim 12, which is a bacterium.

19. The microbial host cell of claim 12, which is a fungus or yeast.

20. A method for producing a modified subtilase, comprising (a) culturing a microbial host cell of claim 17 under conditions conducive to the expression and secretion of the modified subtilase, and (b) recovering the modified subtilase.

* * * * *

SEQUENCE LISTING

<160> NUMBER OF SEQ ID NOS: 12

<210> SEQ ID NO 1
<211> LENGTH: 275
<212> TYPE: PRT
<213> ORGANISM: Bacillus

<400> SEQUENCE: 1

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
```

```
                 195                 200                 205
Leu Pro Gly Asn Lys Tyr Gly Ala Tyr Asn Gly Thr Ser Met Ala Ser
            210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 2
<211> LENGTH: 268
<212> TYPE: PRT
<213> ORGANISM: Bacillus

<400> SEQUENCE: 2

Gln Thr Val Pro Trp Gly Ile Ser Phe Ile Asn Thr Gln Gln Ala His
1               5                   10                  15

Asn Arg Gly Ile Phe Gly Asn Gly Ala Arg Val Ala Val Leu Asp Thr
            20                  25                  30

Gly Ile Ala Ser His Pro Asp Leu Arg Ile Ala Gly Gly Ala Ser Phe
        35                  40                  45

Ile Ser Ser Glu Pro Ser Tyr His Asp Asn Asn Gly His Gly Thr His
    50                  55                  60

Val Ala Gly Thr Ile Ala Ala Leu Asn Asn Ser Ile Gly Val Leu Gly
65                  70                  75                  80

Val Arg Pro Ser Ala Asp Leu Tyr Ala Leu Lys Val Leu Asp Arg Asn
                85                  90                  95

Gly Ser Gly Ser Leu Ala Ser Val Ala Gln Gly Ile Glu Trp Ala Ile
            100                 105                 110

Asn Asn Asn Met His Ile Ile Asn Met Ser Leu Gly Ser Thr Ser Gly
        115                 120                 125

Ser Ser Thr Leu Glu Leu Ala Val Asn Arg Ala Asn Asn Ala Gly Ile
    130                 135                 140

Leu Leu Val Gly Ala Ala Gly Asn Thr Gly Arg Gln Gly Val Asn Tyr
145                 150                 155                 160

Pro Ala Arg Tyr Ser Gly Val Met Ala Val Ala Val Asp Gln Asn
                165                 170                 175

Gly Gln Arg Ala Ser Phe Ser Thr Tyr Gly Pro Glu Ile Glu Ile Ser
            180                 185                 190

Ala Pro Gly Val Asn Val Asn Ser Thr Tyr Thr Gly Asn Arg Tyr Val
        195                 200                 205

Ser Leu Ser Gly Thr Ser Met Ala Thr Pro His Val Ala Gly Val Ala
    210                 215                 220

Ala Leu Val Lys Ser Arg Tyr Pro Ser Tyr Thr Asn Asn Gln Ile Arg
225                 230                 235                 240

Gln Arg Ile Asn Gln Thr Ala Thr Tyr Leu Gly Ser Pro Ser Leu Tyr
                245                 250                 255

Gly Asn Gly Leu Val His Ala Gly Arg Ala Thr Gln
            260                 265

<210> SEQ ID NO 3
<211> LENGTH: 268
```

```
<212> TYPE: PRT
<213> ORGANISM: Bacillus

<400> SEQUENCE: 3

Gln Thr Val Pro Trp Gly Ile Asn Arg Val Gln Ala Pro Ile Ala Gln
1               5                   10                  15

Ser Arg Gly Phe Thr Gly Thr Gly Val Arg Val Ala Val Leu Asp Thr
            20                  25                  30

Gly Ile Ser Asn His Ala Asp Leu Arg Ile Arg Gly Gly Ala Ser Phe
        35                  40                  45

Val Pro Gly Glu Pro Asn Ile Ser Asp Gly Asn Gly His Gly Thr Gln
    50                  55                  60

Val Ala Gly Thr Ile Ala Ala Leu Asn Asn Ser Ile Gly Val Leu Gly
65                  70                  75                  80

Val Ala Pro Asn Val Asp Leu Tyr Gly Val Lys Val Leu Gly Ala Ser
                85                  90                  95

Gly Ser Gly Ser Ile Ser Gly Ile Ala Gln Gly Leu Gln Trp Ala Ala
            100                 105                 110

Asn Asn Gly Met His Ile Ala Asn Met Ser Leu Gly Ser Ser Ala Gly
        115                 120                 125

Ser Ala Thr Met Glu Gln Ala Val Asn Gln Ala Thr Ala Ser Gly Val
    130                 135                 140

Leu Val Val Ala Ala Ser Gly Asn Ser Gly Ala Gly Asn Val Gly Phe
145                 150                 155                 160

Pro Ala Arg Tyr Ala Asn Ala Met Ala Val Gly Ala Thr Asp Gln Asn
                165                 170                 175

Asn Asn Arg Ala Thr Phe Ser Gln Tyr Gly Ala Gly Leu Asp Ile Val
            180                 185                 190

Ala Pro Gly Val Gly Val Gln Ser Thr Val Pro Gly Asn Gly Tyr Ala
        195                 200                 205

Ser Phe Asn Gly Thr Ser Met Ala Thr Pro His Val Ala Gly Val Ala
    210                 215                 220

Ala Leu Val Lys Gln Lys Asn Pro Ser Trp Ser Asn Val Gln Ile Arg
225                 230                 235                 240

Asn His Leu Lys Asn Thr Ala Thr Asn Leu Gly Asn Thr Thr Gln Phe
                245                 250                 255

Gly Ser Gly Leu Val Asn Ala Glu Ala Ala Thr Arg
            260                 265

<210> SEQ ID NO 4
<211> LENGTH: 269
<212> TYPE: PRT
<213> ORGANISM: Bacillus

<400> SEQUENCE: 4

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80
```

-continued

```
Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 5
<211> LENGTH: 274
<212> TYPE: PRT
<213> ORGANISM: Bacillus

<400> SEQUENCE: 5

Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Gly Ile Ile Asp
            20                  25                  30

Thr Gly Ile Ala Ala Ser His Thr Asp Leu Lys Val Val Gly Gly Ala
        35                  40                  45

Ser Phe Val Ser Gly Glu Ser Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Ile Lys Val Leu Asn
                85                  90                  95

Ser Ser Gly Ser Gly Thr Tyr Ser Ala Ile Val Ser Gly Ile Glu Trp
            100                 105                 110

Ala Thr Gln Asn Gly Leu Asp Val Ile Asn Met Ser Leu Gly Gly Pro
        115                 120                 125

Ser Gly Ser Thr Ala Leu Lys Gln Ala Val Asp Lys Ala Tyr Ala Ser
    130                 135                 140

Gly Ile Val Val Ala Ala Ala Gly Asn Ser Gly Ser Ser Gly Ser
145                 150                 155                 160

Gln Asn Thr Ile Gly Tyr Pro Ala Lys Tyr Asp Ser Val Ile Ala Val
                165                 170                 175

Gly Ala Val Asp Ser Asn Lys Asn Arg Ala Ser Phe Ser Ser Val Gly
            180                 185                 190
```

```
Ala Glu Leu Glu Val Met Ala Pro Gly Val Ser Val Tyr Ser Thr Tyr
            195                 200                 205

Pro Ser Asn Thr Tyr Thr Ser Leu Asn Gly Thr Ser Met Ala Ser Pro
            210                 215                 220

His Val Ala Gly Ala Ala Ala Leu Ile Leu Ser Lys Tyr Pro Thr Leu
225                 230                 235                 240

Ser Ala Ser Gln Val Arg Asn Arg Leu Ser Ser Thr Ala Thr Asn Leu
            245                 250                 255

Gly Asp Ser Phe Tyr Tyr Gly Lys Gly Leu Ile Asn Val Glu Ala Ala
            260                 265                 270

Ala Gln

<210> SEQ ID NO 6
<211> LENGTH: 279
<212> TYPE: PRT
<213> ORGANISM: Bacillus

<400> SEQUENCE: 6

Tyr Thr Pro Asn Asp Pro Tyr Phe Ser Ser Arg Gln Tyr Gly Pro Gln
1               5                   10                  15

Lys Ile Gln Ala Pro Gln Ala Trp Asp Ile Ala Glu Gly Ser Gly Ala
            20                  25                  30

Lys Ile Ala Ile Val Asp Thr Gly Val Gln Ser Asn His Pro Asp Leu
        35                  40                  45

Ala Gly Lys Val Val Gly Gly Trp Asp Phe Val Asp Asn Asp Ser Thr
    50                  55                  60

Pro Gln Asn Gly Asn Gly His Gly Thr His Cys Ala Gly Ile Ala Ala
65                  70                  75                  80

Ala Val Thr Asn Asn Ser Thr Gly Ile Ala Gly Thr Ala Pro Lys Ala
                85                  90                  95

Ser Ile Leu Ala Val Arg Val Leu Asp Asn Ser Gly Ser Gly Thr Trp
            100                 105                 110

Thr Ala Val Ala Asn Gly Ile Thr Tyr Ala Ala Asp Gln Gly Ala Lys
            115                 120                 125

Val Ile Ser Leu Ser Leu Gly Gly Thr Val Gly Asn Ser Gly Leu Gln
130                 135                 140

Gln Ala Val Asn Tyr Ala Trp Asn Lys Gly Ser Val Val Val Ala Ala
145                 150                 155                 160

Ala Gly Asn Ala Gly Asn Thr Ala Pro Asn Tyr Pro Ala Tyr Tyr Ser
                165                 170                 175

Asn Ala Ile Ala Val Ala Ser Thr Asp Gln Asn Asp Asn Lys Ser Ser
            180                 185                 190

Phe Ser Thr Tyr Gly Ser Val Val Asp Val Ala Ala Pro Gly Ser Trp
            195                 200                 205

Ile Tyr Ser Thr Tyr Pro Thr Ser Thr Tyr Ala Ser Leu Ser Gly Thr
            210                 215                 220

Ser Met Ala Thr Pro His Val Ala Gly Val Ala Gly Leu Leu Ala Ser
225                 230                 235                 240

Gln Gly Arg Ser Ala Ser Asn Ile Arg Ala Ala Ile Glu Asn Thr Ala
            245                 250                 255

Asp Lys Ile Ser Gly Thr Gly Thr Tyr Trp Ala Lys Gly Arg Val Asn
            260                 265                 270

Ala Tyr Lys Ala Val Gln Tyr
            275
```

<210> SEQ ID NO 7
<211> LENGTH: 269
<212> TYPE: PRT
<213> ORGANISM: Bacillus

<400> SEQUENCE: 7

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 8
<211> LENGTH: 307
<212> TYPE: PRT
<213> ORGANISM: Bacillus

<400> SEQUENCE: 8

```
Met Asn Gly Glu Ile Arg Leu Ile Pro Tyr Val Thr Asn Glu Gln Ile
1               5                   10                  15

Met Asp Val Asn Glu Leu Pro Gly Ile Lys Val Ile Lys Ala Pro
            20                  25                  30

Glu Met Trp Ala Lys Gly Val Lys Gly Lys Asn Ile Lys Val Ala Val
        35                  40                  45

Leu Asp Thr Gly Cys Asp Thr Ser His Pro Asp Leu Lys Asn Gln Ile
    50                  55                  60
```

```
Ile Gly Gly Lys Asn Phe Ser Asp Asp Gly Gly Lys Glu Asp Ala
65                  70                  75                  80

Ile Ser Asp Tyr Asn Gly His Gly Thr His Val Ala Gly Thr Ile Ala
                85                  90                  95

Ala Asn Asp Ser Asn Gly Gly Ile Ala Gly Val Ala Pro Glu Ala Ser
            100                 105                 110

Leu Leu Ile Val Lys Val Leu Gly Gly Glu Asn Gly Ser Gly Gln Tyr
        115                 120                 125

Glu Trp Ile Ile Asn Gly Ile Asn Tyr Ala Val Glu Gln Lys Val Asp
    130                 135                 140

Ile Ile Ser Met Ser Leu Gly Gly Pro Ser Asp Val Pro Glu Leu Glu
145                 150                 155                 160

Glu Ala Val Lys Asn Ala Val Lys Asn Gly Val Leu Val Val Cys Ala
                165                 170                 175

Ala Gly Asn Glu Gly Asp Gly Asp Glu Arg Thr Glu Glu Leu Ser Tyr
            180                 185                 190

Pro Ala Ala Tyr Asn Glu Val Ile Ala Val Gly Ser Val Ser Val Ala
        195                 200                 205

Arg Glu Leu Ser Glu Phe Ser Asn Ala Asn Lys Glu Ile Asp Leu Val
    210                 215                 220

Ala Pro Gly Glu Asn Ile Leu Ser Thr Leu Pro Asn Lys Lys Tyr Gly
225                 230                 235                 240

Lys Leu Thr Gly Thr Ser Met Ala Ala Pro His Val Ser Gly Ala Leu
                245                 250                 255

Ala Leu Ile Lys Ser Tyr Glu Glu Ser Phe Gln Arg Lys Leu Ser
            260                 265                 270

Glu Ser Glu Val Phe Ala Gln Leu Ile Arg Arg Thr Leu Pro Leu Asp
        275                 280                 285

Ile Ala Lys Thr Leu Ala Gly Asn Gly Phe Leu Tyr Leu Thr Ala Pro
    290                 295                 300

Asp Glu Leu
305

<210> SEQ ID NO 9
<211> LENGTH: 281
<212> TYPE: PRT
<213> ORGANISM: Bacillus

<400> SEQUENCE: 9

Ser Asp Gly Thr Asp Thr Ser Asp Asn Phe Glu Gln Trp Asn Leu Glu
1               5                   10                  15

Pro Ile Gln Val Lys Gln Ala Trp Lys Ala Gly Leu Thr Gly Lys Asn
                20                  25                  30

Ile Lys Ile Ala Val Ile Asp Ser Gly Ile Ser Pro His Asp Asp Leu
            35                  40                  45

Ser Ile Ala Gly Gly Tyr Ser Ala Val Ser Tyr Thr Ser Ser Tyr Lys
        50                  55                  60

Asp Asp Asn Gly His Gly Thr His Val Ala Gly Ile Ile Gly Ala Lys
65                  70                  75                  80

His Asn Gly Tyr Gly Ile Asp Gly Ile Ala Pro Glu Ala Gln Ile Tyr
                85                  90                  95

Ala Val Lys Ala Leu Asp Gln Asn Gly Ser Gly Asp Leu Gln Ser Leu
            100                 105                 110

Leu Gln Gly Ile Asp Trp Ser Ile Ala Asn Arg Met Asp Ile Val Asn
```

-continued

```
            115                 120                 125
Met Ser Leu Gly Thr Thr Ser Asp Ser Lys Ile Leu His Asp Ala Val
        130                 135                 140

Asn Lys Ala Tyr Glu Gln Gly Val Leu Val Ala Ala Ser Gly Asn
145                 150                 155                 160

Asp Gly Asn Gly Lys Pro Val Asn Tyr Pro Ala Ala Tyr Ser Ser Val
                    165                 170                 175

Val Ala Val Ser Ala Thr Asn Glu Lys Asn Gln Leu Ala Ser Phe Ser
                180                 185                 190

Thr Thr Gly Asp Glu Val Glu Phe Ser Ala Pro Gly Thr Asn Ile Thr
                195                 200                 205

Ser Thr Tyr Leu Asn Gln Tyr Tyr Ala Thr Gly Ser Gly Thr Ser Gln
        210                 215                 220

Ala Thr Pro His Ala Ala Met Phe Ala Leu Leu Lys Gln Arg Asp
225                 230                 235                 240

Pro Ala Glu Thr Asn Val Gln Leu Arg Glu Glu Met Arg Lys Asn Ile
                    245                 250                 255

Val Asp Leu Gly Thr Ala Gly Arg Asp Gln Gln Phe Gly Tyr Gly Leu
                260                 265                 270

Ile Gln Tyr Lys Ala Gln Ala Thr Asp
        275                 280

<210> SEQ ID NO 10
<211> LENGTH: 345
<212> TYPE: PRT
<213> ORGANISM: Bacillus

<400> SEQUENCE: 10

Leu Arg Gly Leu Glu Gln Ile Ala Gln Tyr Ala Thr Asn Asn Asp Val
1               5                   10                  15

Leu Tyr Val Thr Pro Lys Pro Glu Tyr Glu Val Leu Asn Asp Val Ala
                20                  25                  30

Arg Gly Ile Val Lys Ala Asp Val Ala Gln Asn Asn Phe Gly Leu Tyr
            35                  40                  45

Gly Gln Gly Gln Ile Val Ala Val Ala Asp Thr Gly Leu Asp Thr Gly
        50                  55                  60

Arg Asn Asp Ser Ser Met His Glu Ala Phe Arg Gly Lys Ile Thr Ala
65                  70                  75                  80

Leu Tyr Ala Leu Gly Arg Thr Asn Asn Ala Asn Asp Pro Asn Gly His
                85                  90                  95

Gly Thr His Val Ala Gly Ser Val Leu Gly Asn Ala Thr Asn Lys Gly
            100                 105                 110

Met Ala Pro Gln Ala Asn Leu Val Phe Gln Ser Ile Met Asp Ser Gly
        115                 120                 125

Gly Gly Leu Gly Gly Leu Pro Ala Asn Leu Gln Thr Leu Phe Ser Gln
    130                 135                 140

Ala Tyr Ser Ala Gly Ala Arg Ile His Thr Asn Ser Trp Gly Ala Pro
145                 150                 155                 160

Val Asn Gly Ala Tyr Thr Thr Asp Ser Arg Asn Val Asp Asp Tyr Val
                165                 170                 175

Arg Lys Asn Asp Met Thr Ile Leu Phe Ala Ala Gly Asn Glu Gly Pro
                180                 185                 190

Gly Ser Gly Thr Ile Ser Ala Pro Gly Thr Ala Lys Asn Ala Ile Thr
            195                 200                 205
```

```
Val Gly Ala Thr Glu Asn Leu Arg Pro Ser Phe Gly Ser Tyr Ala Asp
    210                 215                 220

Asn Ile Asn His Val Ala Gln Phe Ser Arg Gly Pro Thr Arg Asp
225                 230                 235                 240

Gly Arg Ile Lys Pro Asp Val Met Ala Pro Gly Thr Tyr Ile Leu Ser
                245                 250                 255

Ala Arg Ser Ser Leu Ala Pro Asp Ser Ser Phe Trp Ala Asn His Asp
                260                 265                 270

Ser Lys Tyr Ala Tyr Met Gly Gly Thr Ser Met Ala Thr Pro Ile Val
            275                 280                 285

Ala Gly Asn Val Ala Gln Leu Arg Glu His Phe Val Lys Asn Arg Gly
        290                 295                 300

Val Thr Pro Lys Pro Ser Leu Leu Lys Ala Ala Leu Ile Ala Gly Ala
305                 310                 315                 320

Ala Asp Val Gly Leu Gly Phe Pro Asn Gly Asn Gln Gly Trp Gly Arg
                325                 330                 335

Val Thr Leu Asp Lys Ser Leu Asn Val
            340                 345

<210> SEQ ID NO 11
<211> LENGTH: 64
<212> TYPE: DNA
<213> ORGANISM: Artificial Sequence
<220> FEATURE:
<223> OTHER INFORMATION: Primer
<220> FEATURE:
<221> NAME/KEY: Misc_feature
<222> LOCATION: (33)..(33)
<223> OTHER INFORMATION: n in position 33 denotes a, t, c, or g
<220> FEATURE:
<221> NAME/KEY: Misc_feature
<222> LOCATION: (42)..(42)
<223> OTHER INFORMATION: n in position 42 denotes a, t, c, or g
<220> FEATURE:
<221> NAME/KEY: Misc_feature
<222> LOCATION: (43)..(43)
<223> OTHER INFORMATION: n in position 43 denotes a, t, c, or g
<220> FEATURE:
<221> NAME/KEY: Misc_feature
<222> LOCATION: (34)..(34)
<223> OTHER INFORMATION: n in position 34 denotes a, t, c, or g

<400> SEQUENCE: 11
gaacgcctct agaagtcgcg ctattaacag csnnctcgag snnggcactt ggcgaagggc    60
ttcc                                                                 64

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
gaactcgatc cagcgatttc                                                20
```